US009746460B2

(12) United States Patent
Nichiporuk et al.

(10) Patent No.: US 9,746,460 B2
(45) Date of Patent: Aug. 29, 2017

(54) METHOD FOR DETECTING THE INTERACTION OF AT LEAST ONE ENTITY WITH A DIELECTRIC LAYER

(71) Applicants: UNIVERSITE CLAUDE BERNARD LYON I, Villeurbanne (FR); ECOLE CENTRALE DE LYON, Ecully (FR); INSTITUT NATIONALE DES SCIENCES APPLIQUEES DE LYON, Villeurbanne (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

(72) Inventors: Tetyana Nichiporuk, Mions (FR); Tetiana Serdiuk, Mions (FR); Volodymyr Lysenko, Villeurbanne (FR); Yuriy Zakharko, Lyons (FR); Alain Geloen, Lyons (FR); Mustapha Lemiti, Lyons (FR)

(73) Assignees: CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 8 days.

(21) Appl. No.: 14/350,489

(22) PCT Filed: Oct. 8, 2012

(86) PCT No.: PCT/FR2012/052274
§ 371 (c)(1),
(2) Date: Apr. 8, 2014

(87) PCT Pub. No.: WO2013/054024
PCT Pub. Date: Apr. 18, 2013

(65) Prior Publication Data
US 2014/0255973 A1   Sep. 11, 2014

(30) Foreign Application Priority Data

Oct. 11, 2011 (FR) ..................................... 11 59174

(51) Int. Cl.
G01N 33/50 (2006.01)
G01N 21/64 (2006.01)
(52) U.S. Cl.
CPC ......... *G01N 33/5091* (2013.01); *G01N 21/64* (2013.01); *G01N 21/6489* (2013.01)
(58) Field of Classification Search
None
See application file for complete search history.

(56) References Cited

U.S. PATENT DOCUMENTS

2010/0035335 A1   2/2010 Lakowicz et al.
2011/0188733 A1   8/2011 Bardos et al.

OTHER PUBLICATIONS

Watts et al. "Optical Biosensor for Monitoring Microbial Cells" (1994), Analytical Chemistry, vol. 66: 2465-2470.*
Duplan et al., A photoluminescence-based quantum semiconductor biosensor for rapid in situ detection of *Escherichia coli*, Sensors and Actuators B: Chemical, Jul. 19, 2011, vol. 160, pp. 46-51 and S1-S4.*
Salamon et al., Coupled Plasmon-Waveguide Resonators: A New Spectroscopic Tool for Probing Proteolipid Film Structure and Properties, Biophysical Journal, 1997, vol. 73, pp. 2791-2797.*
Giebel et al., Imaging of Cell/Substrate Contacts of Living Cells with Surface Plasmon Resonance Microscopy, Biophysical Journal, vol. 76, pp. 509-516.*
Nychyporuk, T., et al. "Strong photoluminescence enhancement of silicon quantum dots by their near-resonant coupling with multi-polar plasmonic hot spots." Nanoscale 3.6 (2011): 2472-2475.*
Biteen, Julie S., et al. "Enhanced radiative emission rate and quantum efficiency in coupled silicon nanocrystal-nanostructured gold emitters." Nano letters 5.9 (2005): 1768-1773.*
International Search Report mailed Jan. 16, 2013, corresponding to International Patent Application No. PCT/FR2012/052274.
Pascal Anger et al.: "Enhancement and Quenching of Single-Molecule Fluorescence", Physical Review Letters, vol. 96, No. 11, Mar. 1, 2006 (Mar. 1, 2006).
F Giorgis et al: "Luminescence processes in amorphous hydrogenated silicon-nitride nanometric multilayers", Physical Review, vol. 60, No. 16, Oct. 15, 1999, pp. 11572-11576.
Pons T et al: "On the quenching of semiconductor quantum dot photoluminescence by proximal gold nanoparticles", Nano Letters, ACS, US, vol. 7, No. 10, Oct. 1, 2007, pp. 3157-3164.
T. Serdiuk et al :"Storage of luminescent nanoparticles in porous silicon: Toward a solid state "golden fleece"", Materials Letters, vol. 65, No. 15-16, Aug. 1, 2011, pp. 2514-2517.
Robertson et al., Gap states in silicon nitride, Applied Physics Letters, 1984, 44, 415-417.

(Continued)

*Primary Examiner* — Robert Yamasaki
(74) *Attorney, Agent, or Firm* — Ladas & Parry LLP

(57) ABSTRACT

The invention relates to a method of detecting the interaction between at least one entity and a dielectric layer containing different electron levels in the energy band gap of the dielectric layer, the method comprising the following steps:
  a) depositing the entity on the dielectric layer;
  b) subjecting the dielectric layer and the entity deposited thereon to exciting electromagnetic radiation that does not give rise to observable luminescence in the entity itself under the conditions implemented in step c); and
  c) detecting the luminescence of the dielectric layer, in which the radiative and non-radiative electron transitions between the energy levels of the band gap have been influenced as a result of its interaction with the entity.

17 Claims, 4 Drawing Sheets

(56) References Cited

OTHER PUBLICATIONS

Nychyporuk et al., Electroless deposition of Ag nanoparticles on the surface of SiNx : H dielectric layers, Solar Energy Materials and Solar Cells, vol. 94, Issue 12, Dec. 2010, pp. 2314-2317.
Mo et al, Luminescence of nanometer-sized amorphous silicon nitride solids, Journal of Applied Physics Letters, 1993, 73, 5185-5188.
Yamaguchi et al, Short lifetime photoluminescence of amorphous-SiNx films, Applied Physics Letters, 2000, vol. 77, No. 23, 3773-3775.
Kang et al, White photoluminescence from SiNx films prepared by plasma enhanced chemical vapor deposition, Proc. of SPIE, vol. 6337, 633710, (2006).

\* cited by examiner (A) (B)

(A) (B)

(A)                  (B)

(A)                  (B)

(A) (B)

METHOD FOR DETECTING THE INTERACTION OF AT LEAST ONE ENTITY WITH A DIELECTRIC LAYER

This application is a 371 of PCT/FR2012/052274, filed on Oct. 8, 2012, which claims priority to French Application No. 1159174, filed Oct. 11, 2011.

The present invention relates to the technical field of detecting luminescence as applied to the biosciences. More precisely, the present invention provides a method of detecting interaction between at least one entity and a luminescent dielectric layer containing various electron levels. Such a method is particularly suitable for studying living cells or cellular organelles such as cellular nuclei and mitochondria.

At present, fluorescent imaging of biological cells is performed by using fluorophores (http://fr.wikipedia.org/wiki/Fluorophore) and II-VI and III-V semiconductor nanoparticles (NPs) (http://fr.wikipedia.org/wiki/Nanocristaux_de_semi-conducteurs). The fluorophores that are used are often of organic nature and they are usually toxic. Furthermore, those molecules lose their luminescence properties, which degrade under the effect of the exciting light, thus limiting the length of time available for observation to a few minutes. II-VI and III-V NPs present the following advantages relative to fluorophores: i) emission wavelength can be controlled by particle size; ii) they give rise to high light yields; and iii) they present greater stability of emission. Nevertheless, such NPs are found to be cytotoxic, because they release toxic ions (e.g. Cd, Se, . . . ) when subjected to photoexcitation.

Patent application US 2010/0035335 uses metallic nanoparticles that amplify either the natural luminescence of cells, or of fluorescent markers incorporated in cells. That document thus concentrates either on amplifying cellular autofluorescence, which leads to a green color only, or else to amplifying coloring agents that have been added to the cells and that have a cytotoxic effect.

Consequently, at present, studying biomolecules by detecting fluorescence requires marked biomolecules to be prepared or leads to monochrome images being obtained that correspond to the natural fluorescence, possibly after amplification, of biomolecules in certain wavelength ranges.

A particular object of the invention is to propose a novel method adapted to studying various biological entities or biomolecules, that is easy to perform and that does not require prior marking of the biological entities or biomolecules.

The method of the invention must thus be simple and competitive compared with prior techniques as summarized above.

In this context, the present invention relates to a method of detecting the interaction between at least one entity and a dielectric layer containing different electron levels in the energy band gap of the dielectric layer, the method comprising the following steps:
 a) depositing the entity on the dielectric layer;
 b) subjecting the dielectric layer and the entity deposited thereon to exciting electromagnetic radiation that does not give rise to observable luminescence of the entity itself under the conditions implemented in step c); and
 c) detecting the luminescence of the dielectric layer, in which the radiative and non-radiative electron transitions between the energy levels of the band gap have been influenced as a result of its interaction with the entity.

More particularly, in the context of the invention, by means of physicochemical interactions with the dielectric layer on which the entity is deposited, the entity is capable of influencing the radiative and non-radiative electron transitions between the energy levels in the band gap of the dielectric layer as caused by the external exciting electromagnetic radiation that is used.

In the method of the invention, it is the luminescence of the dielectric layer as emitted under the influence of the entity that is detected (which entity may in particular be a living cell). The invention makes use of passivation of the dielectric layer by the entity(ies) deposited on the dielectric layer (which entity may in particular be a living cell), thereby increasing the level of radiative recombinations in the layer, thus modifying the luminescence it emits. The method of the invention does not make any use of the plasmon effect, as is used in the method described in patent application US 2010/0035335.

The invention can be better understood from the following description given with reference to the accompanying figures.

In preferred implementations, the dielectric layer is made:
 either of silicon oxide having silicon nanoparticles distributed therein, said layer including Si—H, Si—O—Si, and Si—O—Si bonds; or
 of silicon nitride in which silicon nanoparticles are distributed, said layer including Si—H, Si—N—Si, and N—H bonds; or else
 of a silicon oxy-nitride in which silicon nanoparticles are distributed, said layer including Si—H, Si—N—Si, Si—O—Si, Si—OH, and N—H bonds.

In particularly advantageous manner, the dielectric layer presents the following stoichiometry in terms of atoms of Si, N, and O:
$SiO_x$ with $0<x<2$, $Si_yN_z$ with $1<y<3$ and $0<z<4$, or $Si_tO_uN_v$ with $1<t<3$, $0<u<1$, and $0<v<2$. The stoichiometric amounts given in the context of the invention include the silicon nanoparticles present within the layer.

In general, in such layers, the silicon nanoparticles present a volume fraction lying in the range 5% to 75% relative to the total volume of the dielectric layer (e.g. of the matrix+ silicon nanoparticles). This volume fraction is a function of the stoichiometry of the layer. The dielectric layers richer in Si present a larger volume fraction of Si nanoparticles. The presence of Si nanoparticles can be determined by TEM, the stoichiometry can be determined by spectroscopic techniques on the elements associated with the TEM, and the volume fraction of the silicon particles can be determined by X-ray photoelectron spectroscopy (XPS).

When the dielectric layer is made of silicon oxide with silicon nanoparticles distributed therein, it includes Si—H bonds as a result of hydrogen passivating at least a portion of the interface defects between the silicon oxide matrix and the silicon nanoparticles.

Likewise, when the dielectric layer containing different electron levels in the band gap of the dielectric layer is made up of silicon nitride or silicon oxy-nitride having silicon nanoparticles distributed therein, the layer includes Si—H and N—H bonds corresponding to hydrogen passivating at least some of the interface defects between the silicon nitride or silicon oxy-nitride matrix respectively and the silicon nanoparticles that it contains.

In preferred manner, the dielectric layer is a silicon nitride dielectric layer having silicon nanoparticles distributed therein and that is partially hydrogenated with stoichiometry in terms of silicon atoms and nitrogen atoms written $SiN_{xa}$, where xa lies in the range 0.4 to 0.8.

Figure 1:
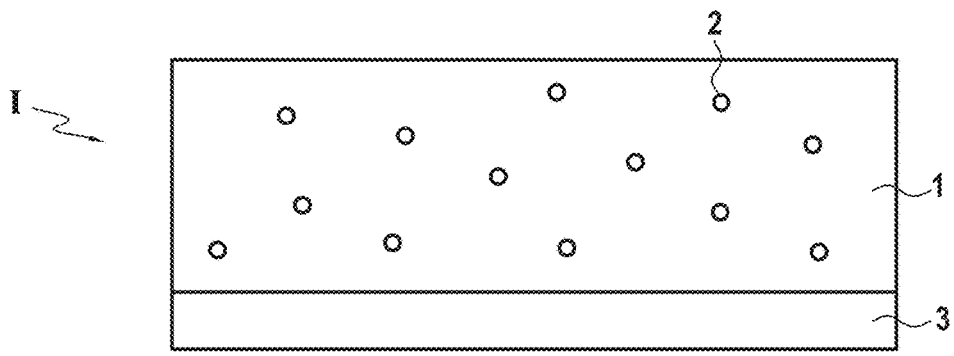
FIG. 1 is a diagrammatic section view of a substrate suitable for use in the context of the invention.

FIG. 1 is a diagrammatic representation of a dielectric layer I constituted by a matrix 1 having silicon particles 2 distributed therein in uniform manner. The matrix 1 may be:
  either silicon oxide including Si—H, Si—O—S, and Si—OH bonds;
  or silicon nitride including Si—H, Si—N—Si and N—H bonds;
  or else silicon oxy-nitride including Si—H, Si—H-Si, Si—O—Si, Si—OH, and N—H bonds.

Figure 2:
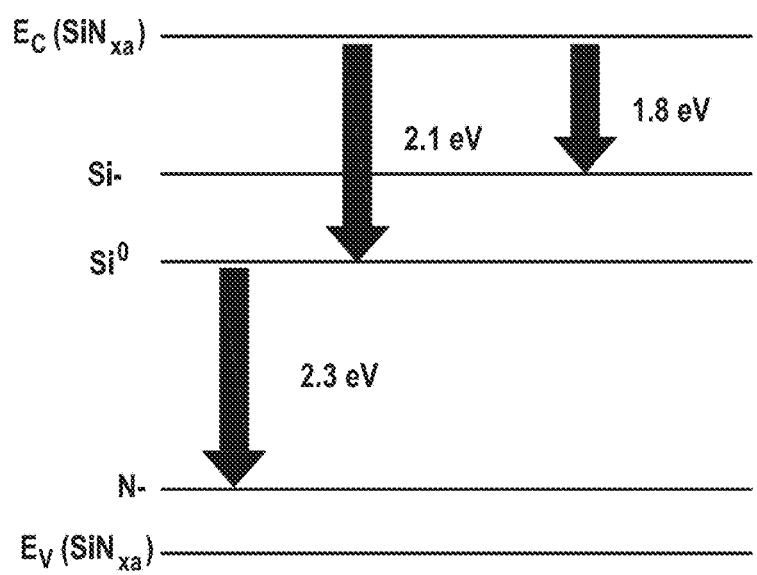
FIG. 2 is an energy state diagram of an $SiN_{xa}$ dielectric layer used in the context of the invention, together with certain possible radiative electron transitions.

FIG. 2 is a diagram of the energy states of an $SiN_{xa}$ dielectric layer as defined above, together with certain potential electron-radiative transitions between the energy levels in the band gap. In accordance with data reported in the literature (J. Robertson et al., Appl. Phys. Lett. 1984, 44, 415-417 and C. Mo et al., J. Appl. Phys. 1993, 73, 5185-5188), the first electron transition ($Ec(SiN_{xa})->Si^-$) corresponds to a red emission relating to the transmission between the conduction band (Ec) of the $SiN_{xa}$ layer and the $S^-$ defect state of the silicon nanoparticles. The second transition (($Ec(SiN_{xa})->Si^0$ corresponding to a yellow emission) takes place between the Ec level of the dielectric matrix and the neutral silicon atoms of the silicon nanoparticles. The third recombination route (giving rise to a green emission) corresponds to the ($Si^0->N^-$) electron transition that takes place between the neutral silicon atoms of the silicon nanoparticles and the $N^-$ defect states of the dielectric matrix. Other recombination routes also exist in the blue emission spectrum for this type of layer (J. Robertson et al., Appl. Phys. Lett. 1984, 44, 415-417 and C. Mo et al., J. Appl. Phys. 1993, 73, 5185-5188).

It is also possible to use other dielectric layers, in particular of organic type, e.g. polymers, and specifically those used in the photovoltaic field.

The interaction between the entity and the dielectric layer makes it possible to reach such transition levels and thus leads to luminescence emission. With living cells in particular, the emission may be different depending on the zone of the cell that is in contact with the dielectric layer, as can be seen below with reference to the figures.

Usually, the entity is placed on the dielectric layer and left for sufficient time to obtain interaction between the entity and the dielectric layer, leading to physicochemical interactions with the dielectric layer on which it is deposited, which interactions influence the radiative and non-radiative electron transitions between the energy levels in the band gap caused by external exciting electromagnetic radiation. Thus, the luminescence emission that is obtained differs from that would be obtained if the entity were deposited on a conventional substrate, such as a glass slide, and such as that obtained with the dielectric layer alone.

The silicon nanoparticles present in the dielectric layer may be in the form of particles that are essentially spherical, small rods, or particles of irregular shape. In general, the particles are essentially spherical. In preferred manner, the silicon nanoparticles have a size of less than 50 nanometers (nm), and advantageously a size lying in the range 1 nm to 20 nm, and preferably lying in the range 1 nm to 7 nm. Usually, the nanoparticles used are essentially spherical, i.e. their shape departs by no more than 10% from that of a perfect sphere. The size of a nanoparticle corresponds to its diameter when the particles are spherical, or to its equivalent diameter when the particles are not spherical. The equivalent diameter of a nanoparticle may be measured by measuring the surface area of each nanoparticle in a transmission electron microscope image. Each nanoparticle is treated as being a perfect sphere, and its equivalent diameter is calculated on the basis of the observed analysis surface area(s) (in cross-section) on the basis of the formula $S=\Pi R^2$, where R corresponds to the radiative of the perfect sphere, and thus of the cross-section, corresponding to the nanoparticle.

In preferred manner, the dielectric layer presents thickness of less than 500 nm, and typically lying in the range 30 nm to 200 nm, and preferably in the range 50 nm to 150 nm, which thickness is naturally appropriate for the size of the silicon nanoparticles that are present.

In general, the dielectric layer is deposited on a substrate 3 acting as a medium, as shown in FIG. 1. In general, such substrates are of the glass or quartz slide type or else they are made of silicon, or more generally of any medium capable of supporting the method of depositing the dielectric layer.

In the context of the invention, the dielectric layers may be obtained by a chemical vapor deposition (CVD) method, and in particular by a plasma enhanced chemical vapor deposition method, named PECVD.

CVD is performed by causing various ingredients to react in a vapor phase. The ingredients are created by causing several species to dissociate. Those reactions require an energy source, which may be heat energy, but which could also be energy supplied by a plasma or from some other energy source.

When the matrix is made of silicon oxide, deposition is performed using a gaseous mixture made up of silane ($SiH_4$) and of nitrogen protoxide ($N_2O$), possibly in a vector gas of the argon, helium, or hydrogen type. When the matrix is made of silicon nitride, deposition is performed using a gas mixture containing $SiH_4$, ammonia ($NH_3$), or nitrogen ($N_2$) acting as precursor gases. When the matrix is made of silicon oxy-nitride, deposition is performed using a gas mixture made up of $SiH_4$, $NH_3$ (or $N_2$), and $N_2O$.

The various stoichiometric amounts are obtained by varying the ratios of the precursor gases. Different deposition times determine different thicknesses.

The layers deposited by CVD directly contain silicon nanoparticles incorporated in their material. The size and the density of the Si nanoparticles depend mainly on the stoichiometry of the layers. For example, with a silicon nitride matrix, the richer the layers are in Si, the greater the size of the nanoparticles. The richer the layers are in nitrogen, the smaller the size of the nanoparticles and the lower their density. As an indication, for an $SiN_{xa}$ matrix where xa lies in the range 0.4 to 0.8, the size of the nanoparticles will usually lie in the range 1 nm to 7 nm, and more specifically will be about 3 nm to 4 nm.

With PECVD, such deposition may be performed at a temperature lying in the range 50° C. to 500° C., and typically being about 370° C. The pressure, the frequency, and the power injected to generate the plasma, and also the gas flow rate, depend on the reactor used and should be adapted by the person skilled in the art.

The resulting deposited layers contain Si nanoparticles incorporated in the matrix of silicon oxide, of silicon nitride, or of silicon oxy-nitride, as a function of the gas mixture used. Such layers are particularly heterogeneous, which is why mention is made of the presence of Si—H and Si—OH bonds when using silicon oxide, of Si—H and N—H bonds when using silicon nitride, and the presence of Si—H, Si—OH, and N—H bonds when using silicon oxy-nitride. The preparation of such dielectric layers is described in particular by J-F. Lelievre in "Elaboration de SiNx:H par PECVD: optimisation des propriétés optiques, passivantes et structurales pour applications photovoltaïques" [Preparation of SiNx:H by PECVD: optimizing optical, passivating, and structural properties for photovoltaic applications], INSA Lyon thesis, 2007, p. 187, and by J. Dupuis in "Elaboration et charactérisation de couches SiOxNy:H et SiNx:H réalisées par méthode PECVD: application à la face arrière des cellules photovoltaïques en Silicium" [Preparing and characterizing SiOxNy:H and SiNx:H layers made by PECVD: application to the rear faces of silicon photovoltaic cells], INSA Lyon thesis, 2009, p. 161, to which reference may be made for further details.

It is also possible for deposition to be performed by other chemical vapor deposition techniques well known to the person skilled in the art, specifically the UV(Hg) photo assisted chemical vapor deposition (UVCVD) technique, the atmospheric chemical vapor deposition (APCVD) technique, or the low pressure chemical vapor deposition (LP-CVD) technique. For further details on these techniques, reference may be made to G. S. May, S. M. Sze, Fundamentals of semiconductor fabrication, 2008, Wiley-Interscience, ISBN-0471-23279-3.

The method of the invention may be applied to any type of biological entity, in particular to molecules forming part of the composition of cells, such as proteins, lipids (phospholipids or glycolipids), DNA, RNA, or indeed cells or more generally cellular organelles such as nuclei and mitochondria. The method of the invention may be used for any type of substance (goods in the biomedical, agri-food, cosmetics, perfumery, etc. fields) that may have a physicochemical interaction with the dielectric layer, thereby influencing radiative and non-radiative electron transitions between the energy levels in the band gap as caused by external exciting electromagnetic radiation. Once the entities have been placed on the layer, they influence the luminescence emission that is obtained as a result of electromagnetic excitation, such as light radiation, and they lead to different sets of colors being emitted by the dielectric layers used, in particular the layers of silicon oxide, of silicon nitride, or of silicon oxy-nitride having Si nanoparticles incorporated therein and as defined in the context of the invention.

It is possible to deposit a single entity on the dielectric layer (in particular a single cell), or a population of entities (in particular a cell culture). The entity may be deposited in the form of a solution or a suspension in a suitable solvent, or "as is". In general, the duration of contact between the entity and the dielectric layer prior to measuring luminescence, and prior to excitation if excitation is not performed using natural light, is preferably longer than 10 seconds (s), or indeed longer than 1 hour (h) or 1 day (d), where these times are a function of the entity under study. For example, for certain types of cell, times longer than one or several days can be necessary, in particular for a multicolor image to appear.

The method of the invention is particularly advantageous when the entity is a living cell. Under such circumstances, the living cell may be deposited and cultured directly on the dielectric layer. For this purpose, any culture medium well known to the person skilled in the art may be used. Rinsing may preferably be performed prior to measuring luminescence, or indeed prior to applying excitation if excitation is not performed using natural light. Prior to detection, it may be useful to fix the cell(s) using techniques that are well known to the person skilled in the art, e.g. rinsing with ethanol.

The method of the invention, in particular when the entity is a cell or a cell nucleus or a mitochondrion, may be used to perform cell differentiation, to diagnose a pathology, and in particular a cancer, or indeed to evaluate the effectiveness of a treatment. In these various circumstances, the luminescence emitted by the cell or the cellular organelle under study is generally compared with reference luminescence: for example a healthy cell or organelle when diagnosing a pathology, or a cell or an organelle before treatment when evaluating the effectiveness of a treatment. Because of the modifications that take place within the cell or the cellular organelle, its interaction with the dielectric layer will be different, leading to different luminescence being emitted under electromagnetic excitation.

More generally, mention may be made of the following applications for the method of the invention:
    viewing biological cells in multiple colors, without adding specific fluorescent agents;
    identifying cells, and in particular distinguishing between healthy cells and cancerous cells; and
    detecting the metabolic state (in particular distinguishing between mitosis, apoptosis, . . . ) of a cell culture, or of certain cells in a population of cells.

Whatever, the implementation of the invention, provision may be made to ensure that the dielectric layer does not include any metal particles, neither within its bulk nor on its surface. Nevertheless, although these variants are preferred, it is possible to incorporate nanoparticles of silver, for example, within or on the surface of the dielectric layer. For the preparation of such media, reference may be made for example to Solar Energy Materials and Solar Cells, Volume 94, Issue 12, December 2010, pp. 2314-2317.

Furthermore, whatever the implementation of the invention, detection may be performed without adding luminescent agent to the entity. i.e. in particular, without prior marking of the entity.

In the context of the invention, the exciting electromagnetic radiation is usually radiation of light that is visible to the human eye, infrared radiation, ultraviolet radiation, or X-ray radiation. Advantageously, it is possible to use electromagnetic radiation in the wavelength range 250 nm to 700 nm.

The means for detecting luminescence may be a charge-coupled device (CCD) sensor connected to a computer system for processing the resulting image. Detection itself is preferably performed in the wavelength range 300 nm to 2000 nm.

Advantageously, with the method of the invention it is possible that the luminescence of the dielectric layer is detected in step c) in the form of an image in a plurality of colors.

It is possible to use the invention in biology or in medicine where such use consists merely in replacing the glass substrates that are conventionally used as cell culture media (for observation using an optical microscope), with substrates, in particular substrates made of glass, carrying a dielectric layer and in particular a layer of silicon oxide, of silicon nitride, or of silicon oxy-nitride with Si nanoparticles being incorporated therein and as defined in the context of the invention.

The method of the invention offers novel approaches in the field of cellular imaging, and makes it possible in particular to view cells (or more generally to view biological entities) in multiple colors, without requiring the use of any fluorescent agents such as fluorophores or fluorescent nanoparticles that disturb or completely change the normal operation of cells or cellular organelles.

The method of the invention makes it possible to perform effective in vitro visualization of a biological entity for a wide variety of applications in biology or medicine. The method of the invention is particularly suitable for viewing and studying cells, in particular in the form of cell cultures, or indeed cellular organelles such as nuclei or mitochondria that may be isolated from the cells.

The examples given below serve to illustrate the invention but they have no limiting character.

Substrate Preparation

Substrates constituted by a glass slide covered in a partially hydrogenated dielectric layer of silicon nitride with silicon nanoparticles distributed therein, referred to below as "$SiN_{xa}$/glass" substrates have been made by PECVD in a semi-industrial reactor operating at low frequency (440 kilohertz (kHz)). A mixture of gases made up of silane ($SiH_4$) and of ammonia ($NH_3$) was introduced into the reactor at a flow rate of 800 standard cubic centimeters per minute (sccm). The pressure and the injected power were set respectively at 1.5 Torr and 0.26 watts per square centimeter ($W/cm^2$). Deposition was performed at a temperature of 370° C. Deposition rate was about 25 nanometers per minute (nm/min) for the $SiN_{xa}$ layer, with xa=0.5. Deposition time was adjusted to obtain thicknesses of 60 nm, 100 nm, 150 nm, and 200 nm.

Figure 3:
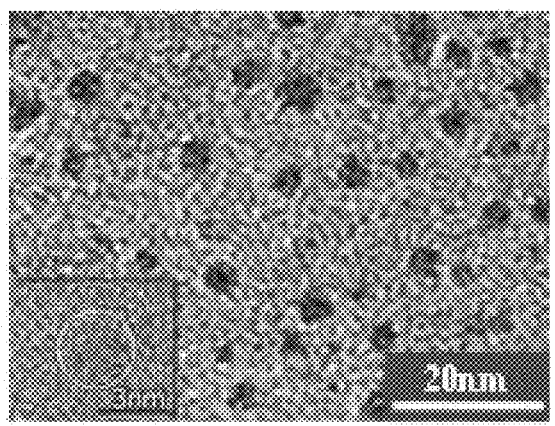
FIG. 3 is a photograph in plan view taken with a transmission electron microscope (TEM) showing an $SiN_{xa}$ dielectric layer with xa=0.5 deposited on a glass slide obtained in accordance with the example below.

The ratio of the flow rates of ammonia and silane gases in the gas flow determines the stoichiometry of the deposited dielectric layer (including its silicon nanoparticles), which ratio was thus equal to 5. The deposit had a thickness lying in the range 60 nm to 200 nm, depending on deposition time. FIG. 3 is a TEM photograph of the resulting deposit and it shows the presence of silicon nanoparticles having a diameter lying in the range 2 mm to 4 mm within the silicon nitride matrix.

Detecting Fluorescence

All of the photographs shown in FIGS. 4 to 8 were obtained with a fluorescence microscope (Leica DMI 4000B) with a combination of filters enabling excitation in the UV/violet range (2.7 electron volts (eV) to 3.5 eV) with an observation spectral range of less than 2.64 eV. It has been found that the colors do not change if the stoichiometry remains the same while thicknesses increase. The figures shown were taken with a layer having a thickness of 60 nm as described above. It has also been found that with stoichiometry as obtained with an ammonia/silane gas flow rate ratio of 3, comparable results were obtained.

Cell cultures of 3T3-L1 fibroblasts (American Type Culture Collection, Manassas, Va., USA) were prepared on $SiN_{xa}$/glass substrates as described above in a Dulbecco's modified Eagle's medium (DMEM) having added thereto 10% newborn calf serum, 4 millimoles (mM) of glutamine, 4 nanomoles (nM) of insulin (Actrapid Human; Novo), 10 mM Hepes, 30 milligrams (μg) sodium ascorbate, 100 international units (IU) of penicillin, 100 μg of streptomycin, and 0.25 milligrams per liter (mg/L) of amphotoercine B at 37° C. in an atmosphere saturated with water with 5% $CO_2$ in air, in a Heraeus (BB16) incubator. After the incubation period and before microscope observation, the cells were rinsed twice with pure ethanol and were fixed to the substrate.

Figure 4:
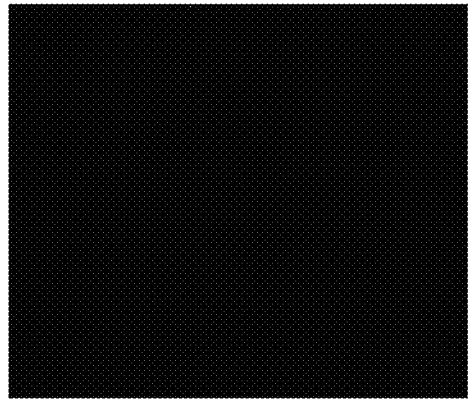
FIG. 4 shows photographs obtained with 3T3 fibroblasts deposited on a glass medium (A) and a glass medium covered in a layer of $SiN_{xa}$ (B) obtained in accordance with the example below.
Figure 4:
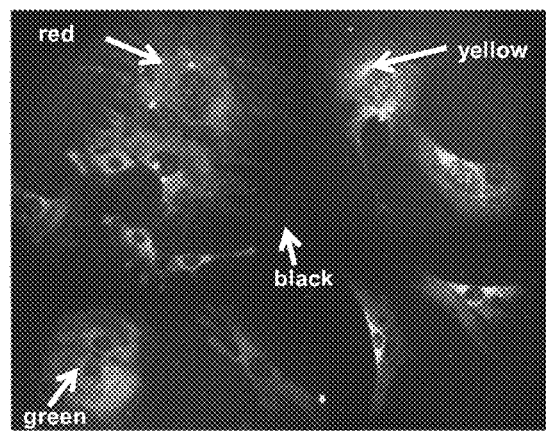

The images shown in FIG. 4 show the effectiveness of the method of the invention for fluorescent viewing of biological cells without any specific additional agent. The two images were obtained under the same optical acquisition conditions. It can be seen (FIG. 4(A)) that there is no natural fluorescence (green color) of 3T3-L1 cells fixed on ordinary glass-based media. In contrast, the same cells spread on substrates obtained as described above produced fluorescence that is clearly visible (FIG. 4(B)) with a multi-color image having red/yellow and green zones. In FIG. 4(B), the locations where cells are not seen correspond to the $SiN_{xa}$ layer in the absence of cells. Under the same experimental conditions, the intensity of the luminescence of the layers on their own is thus very weak, thus demonstrating that the deposited cells not only give rise to a given set of colors, but also that they passivate non-radiative states.

The colors obtained do indeed correspond to possible transitions such as those shown in FIG. 2. Furthermore, the cell has different influences on the substrate such that it is possible to distinguish between the various compartments of the cell since they correspond to fluorescence being emitted in different colors. It is thus possible to distinguish the nucleus, the endoplasmic reticulum, and the cytoplasm. Furthermore, the intensity of the detected fluorescence is well above that obtained with the autofluorescence signal of the cells (green only) as obtained under the same acquisition conditions in terms of acquisition time and excitation intensity. These results show that it is possible to detect cells with the method of the invention without using a fluorophore, and without additional luminescent nanoparticles.

Figure 5:
FIG. 5 shows photographs obtained with healthy human epithelial cells (A) and with cancerous epithelial cells (B) deposited on a glass medium covered in a layer of $SiN_{xa}$ in accordance with the example below.
Figure 5:
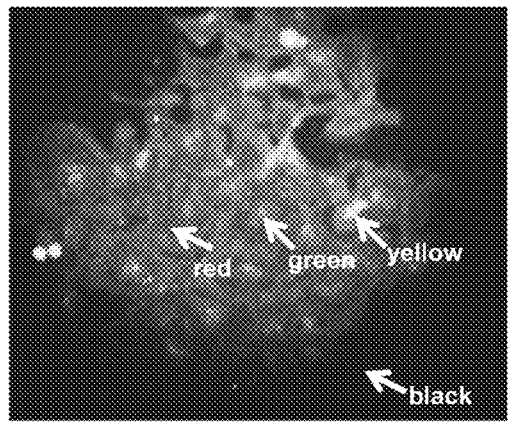
Figure 6:
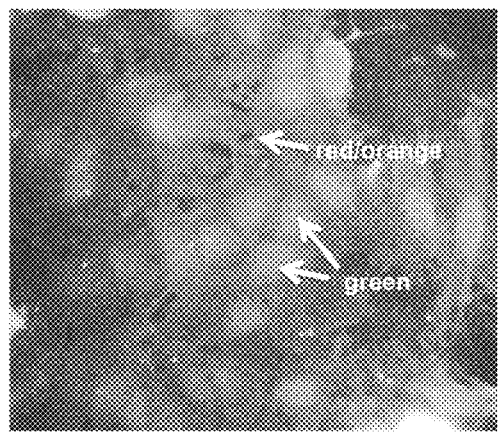
FIG. 6 shows photographs obtained with different cancer cells deposited on a glass medium covered in a layer of $SiN_{xa}$ obtained in accordance with the example below: (A) HUH7 cancer cells, and (B) sHSC cancer cells.
Figure 6:
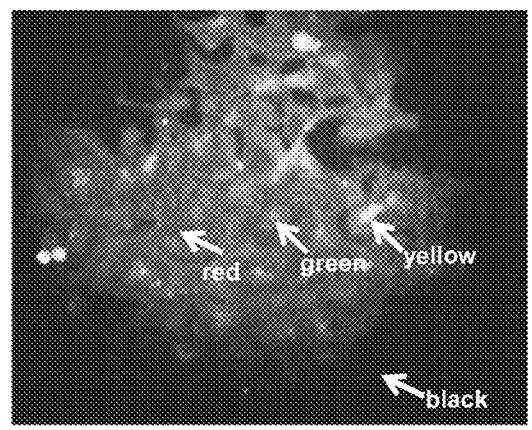

FIGS. 5 and 6 reveal the different fluorescence obtained with cells that are different, either because the cells are of different kinds (FIG. 6) or because their healthy versus cancerous natures differ (FIG. 5).

When cultured on the same $SiN_{xa}$/glass medium as described above, a very marked difference is observed between healthy cells and cancerous cells (FIG. 5). Since the cells are of different natures, their interactions with the dielectric layer are different, thereby leading to different fluorescence emissions, thus making it possible to distinguish between two cell lines even though they are of the same type (epithelial cells). The only difference is their tumorigenicity: (A) immortalized human epithelial cells; (B) HSC epithelial cancer cells.

In the same manner, it is possible to distinguish between cancer cells of different natures as shown in FIG. 6.

Figure 7:
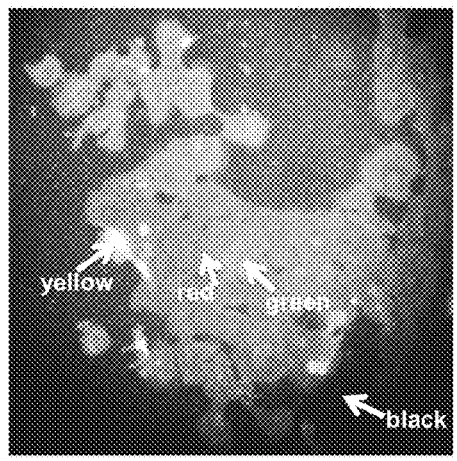
FIG. 7 shows photographs obtained in two different tests with sHSC cancer cells deposited on a glass medium covered in a layer of $SiN_{xa}$ obtained in accordance with the example below.
Figure 7:
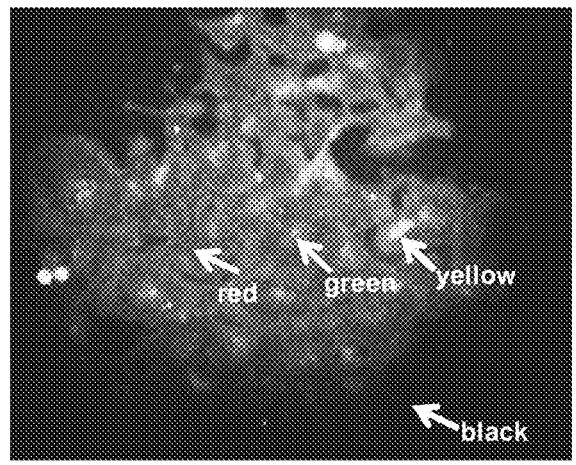
Figure 8:
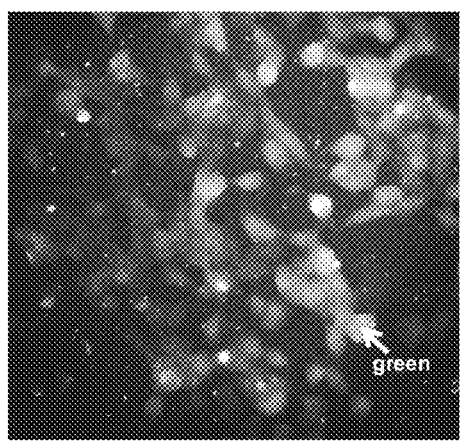
FIG. 8 shows photographs obtained in two different tests with healthy epithelial cells deposited on a glass medium covered in a layer of $SiN_{xa}$ obtained in accordance with the example below.
Figure 8:
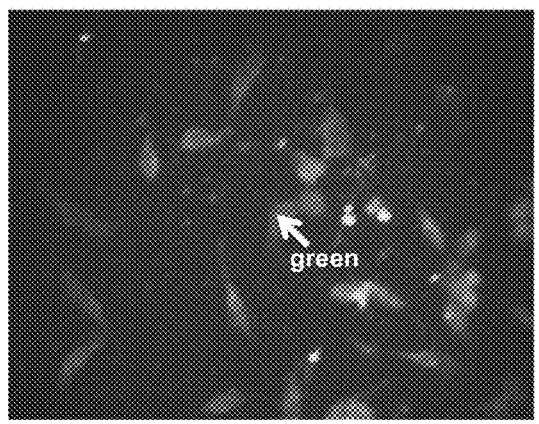

FIGS. 7 and 8 show the reproducibility of the photographs that are obtained in two different tests performed on the same cells and on the same medium covered in an $SiN_{xa}$/glass layer as described above.

The invention claimed is:

1. A method of detecting the interaction between at least one entity and a dielectric layer containing different electron levels in the energy band gap of the dielectric layer, the method comprising the following steps:
  a) depositing the at least one entity on the dielectric layer;
  b) subjecting the dielectric layer and the at least one entity deposited on the dielectric layer to exciting electromagnetic radiation that does not give rise to observable luminescence of the at least one entity itself under the conditions implemented in step c); and
  c) detecting the luminescence of the dielectric layer, in which the radiative and non-radiative electron transitions between the energy levels of the band gap have been influenced as a result of its interaction with the at least one entity;
  wherein the dielectric layer is made of a member selected from the group consisting of:
  silicon oxide, in which silicon nanoparticles are distributed, and wherein said dielectric layer comprises Si—H, Si—O—Si, and Si—OH bonds, with a stoichiometry, in terms of atoms of Si and O, of SiOx, with $0<x<2$;
  silicon nitride, in which silicon nanoparticles are distributed, and wherein said dielectric layer comprises Si—H, Si—N—Si, and N—H bonds, with a stoichiometry, in terms of atoms of Si and N of SiyNz, with $1<y<3$ and $0<z<4$; and
  a silicon oxy-nitride, in which silicon nanoparticles are distributed, and wherein said dielectric layer comprises Si—H, Si—N—Si, Si—O—Si, Si—OH, and N—H bonds, with a stoichiometry, in terms of atoms of Si, N, and O, of SitOuNv, with $1<t<3$, $0<u<1$, and $0<v<2$;
  wherein the at least one entity is a biological entity.

2. The method according to claim 1, wherein, by physicochemical interactions with the dielectric layer on which the at least one entity is deposited, the at least one entity is capable of influencing the radiative and non-radiative electron transitions between the energy levels in the band gap as caused by the exciting electromagnetic radiation.

3. The method according to claim 1, wherein the silicon nanoparticles have a size in a range from 1 nm to 20 nm.

4. The method according to claim 3, wherein the silicon nanoparticles have a size in a range from 1 nm to 7 nm.

5. The method according to claim 1, wherein the dielectric layer has a thickness of less than 500 nm.

6. The method according to claim 5, wherein the dielectric layer has a thickness in a range from 50 to 150 nm.

7. The method according to claim 1, wherein the dielectric layer is a dielectric layer of silicon nitride having silicon nanoparticles distributed therein, and that is partially hydrogenated, in which the stoichiometry in atoms of silicon and atoms of nitrogen is SiNxa, where xa is in a range from 0.4 to 0.8.

8. The method according to claim 1, wherein the dielectric layer does not include any metallic particles, neither in material of the dielectric layer, nor on a surface of the dielectric layer.

9. The method according to claim 1, wherein the exciting electromagnetic radiation is selected from the group consisting of radiation of light visible to the human eye, infrared radiation, ultraviolet radiation, and X-ray radiation.

10. The method according to claim 1, wherein the luminescence of the dielectric layer is detected in step c) in the form of an image having a plurality of colors.

11. The method according to claim 1, wherein the dielectric layer is obtained by a plasma excited chemical vapor deposition technique.

12. The method according to claim 1, wherein detection is carried out without adding a luminescent agent to the at least one entity.

13. The method according to claim 1, wherein the biological entity is a living cell.

14. The method according to claim 1, wherein the biological entity is a living cell that is deposited and cultured on the dielectric layer.

15. The method according to claim 1, wherein the biological entity is a molecule forming part of a cell or a cellular organelle.

16. The method according to claim 15, wherein the biological entity is a member selected from the group consisting of a protein, a lipid, a DNA, a RNA, a nucleus, and a mitochondrion.

17. The method according to claim 1, wherein the silicon nanoparticles present a volume fraction lying in a range of 5% to 75% relative to a total volume of the dielectric layer.

* * * * *